United States Patent
Um

(10) Patent No.: US 9,340,951 B2
(45) Date of Patent: May 17, 2016

(54) APPARATUS FOR COLLECTING SURFACE SEABED SEDIMENT AND APPARATUS FOR COLLECTING SEABED SEDIMENT USING THE SAME

(71) Applicant: Korea Institute of Geoscience and Mineral Resources, Daejeon (KR)

(72) Inventor: In Kwon Um, Daejeon (KR)

(73) Assignee: KOREA INSTITUTE OF GEOSCIENCE & MINERAL RESOURCES, Daejeon (KR)

( * ) Notice: Subject to any disclaimer, the term of this patent is extended or adjusted under 35 U.S.C. 154(b) by 0 days.

(21) Appl. No.: 14/541,333

(22) Filed: Nov. 14, 2014

(65) Prior Publication Data

US 2016/0076218 A1    Mar. 17, 2016

(30) Foreign Application Priority Data

Sep. 16, 2014    (KR) .................. 10-2014-0122750

(51) Int. Cl.
*E02F 3/92*     (2006.01)
*E02F 3/88*     (2006.01)
*E02F 7/00*     (2006.01)

(52) U.S. Cl.
CPC ............ *E02F 3/9268* (2013.01); *E02F 3/8858* (2013.01); *E02F 3/92* (2013.01); *E02F 7/005* (2013.01)

(58) Field of Classification Search
CPC ............. G01N 1/08; G01N 1/04; E21B 7/26; E21B 11/02; E02F 3/8858; E02F 7/005
USPC ............. 175/20, 58; 37/307, 341; 73/864.74, 73/864.73, 864, 91
See application file for complete search history.

(56) References Cited

U.S. PATENT DOCUMENTS

| | | | |
|---|---|---|---|
| 2,005,819 A * | 6/1935 | Blanchard ............... | E21B 25/14 175/250 |
| 3,805,900 A * | 4/1974 | Sainsbury ............... | E21B 25/04 175/20 |
| 3,833,075 A * | 9/1974 | Bachman ............... | E21B 25/18 175/20 |
| 7,828,079 B2 * | 11/2010 | Oothoudt ............. | E21B 27/005 166/99 |

FOREIGN PATENT DOCUMENTS

| KR | 10-0727590 B1 | 6/2007 |
|---|---|---|
| KR | 10-0978143 B1 | 8/2010 |
| KR | 10-1029693 B1 | 4/2011 |
| KR | 10-1062218 B1 | 8/2011 |
| KR | 10-2013-0042414 A | 4/2013 |

* cited by examiner

*Primary Examiner* — John G Weiss
(74) *Attorney, Agent, or Firm* — Dentons US LLP

(57) ABSTRACT

An apparatus for collecting surface seabed sediment. A cylindrical cover part is connected to a trigger, has an open bottom end, and has a position maintaining part disposed therein. A holder part is coupled with the position maintaining part, and has a longitudinal hollow space defined therein. A pipe-shaped sediment collecting part is detachably coupled at one end with a bottom end of the cover part, and has a receiving space defined therein, such that seabed sediment is accommodated within the receiving space. A head part is disposed at one end thereof on the other end of the sediment collecting part, has a hollow space defined therein, and has an insert blade on a periphery. A catcher part is disposed on an inner circumference of the head part, and allows seabed sediment to enter the receiving space of the sediment collecting part while preventing the collected sediment from being lost.

9 Claims, 9 Drawing Sheets

APPARATUS FOR COLLECTING SURFACE SEABED SEDIMENT AND APPARATUS FOR COLLECTING SEABED SEDIMENT USING THE SAME

RELATED APPLICATION DATA

This application is a continuation of Korean Patent Application No. KR 2014-0122750 filed Sep. 16, 2014, the entirety of which is incorporated herein by reference to the extent permitted by law.

BACKGROUND OF THE INVENTION

1. Field of the Invention

The present invention relates, in general, to an apparatus for collecting surface seabed sediment and an apparatus for collecting seabed sediment using the same. More particularly, the present invention relates to an apparatus for collecting surface seabed sediment able to collect sediment from a surface seabed by descending in the direction perpendicular to the seabed while preventing upper sediment from being disturbed in the surface seabed and concurrently to collect sediment from a deep region of the seabed, an apparatus for collecting seabed sediment using the same.

2. Description of the Related Art

The most fundamental and important sampling method in oceanographic research is to collect a sediment sample from a seabed. The collected sample provides raw materials for extensive research in a variety of fields, such as geology, geotechnology, geochemistry and benthology.

In particular, the seabed sediment is used as a sample for paleoenvironmental research since it properly retains information about the environmental changes of the earth. Additionally, seabed sediment is also in the limelight as an energy source since it contains submarine mineral resources (gas hydrates, manganese modules, phosphate rocks, marine aggregates, etc.).

Furthermore, seabed sediment is used as a sample when studying marine pollution or land-based pollutants.

Since seabed sediment can be used for a variety of purposes, the necessity to collect a seabed sediment sample is increasing. In addition, a variety of types and shapes of apparatus for collecting seabed sediment samples are commercially distributed.

Examples of the apparatus for collecting seabed sediment include: a grab, a dredge, a piston corer, a gravity corer, a multi-corer, and the like.

The grab is typically used at the coast in order to dredge seabed sediment. The grab is also used for dredging for the purpose of maintaining waterways. The dredge collects seabed sediment while being carried on a vessel. The dredge is typically used for collecting seabed rocks, such as manganese modules and solidified phosphate rocks, contained in seabed sediment.

The piston corer has an outer body functioning as a cylindrical body and a piston body received in the outer body, the piston body performing a piston action. A trigger weight disposed at the lateral bottom portion of the piston corer first touches the seabed, at which point in time a wound cable is unwound such that the piston corer instantaneously freely falls to be stuck into a deep region of the seabed. In this manner, seabed sediment is collected by the piston corer.

The length of the piston corer can be fabricated according to the length of a vessel or the height of a winch. It is typical that the length of the piston corer ranges from 3 to 15 m.

The gravity corer is configured such that a plastic pipe is fitted into an iron pipe functioning as a cylindrical body. The gravity corer is stuck into the seabed simply due to the weight of the gravity corer in order to collect seabed sediment.

The box corer is in the shape of a box with open top and bottom ends, with a collecting body formed of metal being positioned between the top and bottom ends inside the box. When a frame is seated on the seabed, the collecting body moves toward seabed sediment, and a shovel-shaped bottom lid moves downwards to collect the seabed sediment.

The multi corer has 4 to 8 collector bodies disposed within a frame. The collector bodies are in the shape of pipes, and are formed of plastic. The multi corer can collect seabed sediment to a depth of about 50 cm from the seabed surface.

When the frame of the multi corer is seated on the seabed surface, the multi corer is triggered, and the collector bodies move toward seabed sediment to collect the seabed sediment.

The piston corer and the gravity corer are used for collecting seabed sediment for the purpose of studies of paleoenvironment or submarine mineral resources of deep sea environments. Sediment is collected from a surface seabed using the multi corer or the box corer in order to be used as a sample from which the recent deposition environment can be known.

In particular, the operation of collecting seabed sediment must be performed twice at the same point for sediment recovered perfectly including surface sample, thereby increasing the cost and time of investigation. In addition, when the piston corer (or the gravity corer) is used, upper sediment is disturbed due to an impact caused by the corer colliding against the sediment, thereby lowering the precision of the investigation, which is problematic.

In order to solve the foregoing problems, Korean Patent No. 10-0978143 disclosed a technology of collecting seabed sediment able to collect sediment from a deep region of the seabed using a piston corer and collect sediment from a surface seabed using a trigger weight as a surface sediment-collecting corer.

However, in the related art, when the surface sediment-collecting corer is fallen freely in order to collect sediment from the surface seabed, it is difficult to make the surface sediment-collecting corer precisely fall in the vertical direction onto the seabed since ocean bottom current.

Therefore, there are potential errors when calculating the deposition rate from the collected sediment sample or when performing high-definition analysis on the collected sediment sample.

The information disclosed in the Background of the Invention section is only for the enhancement of understanding of the background of the invention, and should not be taken as an acknowledgment or as any form of suggestion that this information forms a prior art that would already be known to a person skilled in the art.

RELATED ART DOCUMENT

Patent Document 1: Korean Patent No. 10-0978143

SUMMARY OF THE INVENTION

Accordingly, the present invention has been made keeping in mind the above problems occurring in the related art, and the present invention is intended to propose an apparatus for collecting surface seabed sediment able to not only collect sediment from a surface seabed but also function as a trigger weight without an additional operation when collecting sediment from a deep region of the seabed using sediment sampler which has trigger system.

The present invention is also intended to propose an apparatus for collecting surface seabed sediment able to vertically fall onto a seabed and collect sediment from the surface of the seabed in a precise and safe manner without causing disturbances.

The present invention is also intended to propose an apparatus for collecting seabed sediment able to collect sediment not only from the surface of a seabed, but also from a deep region of the seabed.

The objects of the invention are not limited to the above-described objects but other objects can be clearly understood to those skilled in the art in conjunction with the following description.

In order to achieve the above object, according to one aspect of the present invention, there is provided an apparatus for collecting surface seabed sediment including: a cylindrical cover part connected to a trigger, and having an open bottom end, the cover part comprising a position maintaining part disposed therein; a holder part coupled with the position maintaining part, and having a longitudinal hollow space defined therein; a pipe-shaped sediment collecting part, one end of the sediment collecting part being detachably coupled with a bottom end of the cover part, the sediment collecting part having a receiving space defined therein, such that seabed sediment is accommodated within the receiving space; a head part, one end of the head part being disposed on the other end of the sediment collecting part, the head part having a hollow space defined therein, and comprising an insert blade on a periphery, the insert blade enabling the head part to be inserted into a surface of a seabed; and a catcher part disposed on an inner circumference of the head part, wherein the catcher part allows seabed sediment to enter the receiving space of the sediment collecting part while preventing the collected seabed sediment from being lost.

The cover part may include a pair of support members, wherein one end of each of the support members is engaged with an inner surface of a top end of the cover part, the support members are spaced apart from a central portion of the cover part and are disposed in a direction perpendicular to a top surface of the cover part, and the position maintaining part is disposed at the other end of each of the support members. The sediment collecting part is coupled with the position maintaining part by means of the holder part, and is positioned such that a longitudinal direction of the sediment collecting part is in a direction of the force of gravity.

The position maintaining part may include: a circular belt member engaged with the other end of each of the support members; a circular belt-shaped first rotary member disposed inside the belt member, the first rotary member being rotatably coupled with opposite portions of the circular belt member; and a circular belt-shaped second rotary member disposed inside the first rotary member, the second rotary member being rotatably coupled with opposite portions of the first rotary member. The direction in which the first rotary member rotates is perpendicular to a direction in which the second rotary member rotates, and an outer circumference of the holder part is coupled with an inner circumference of the second rotary member.

The holder part may have a holding groove on an inner circumference of a bottom end thereof, and the sediment collecting part has a holding flange on an outer circumference of one end thereof, wherein the holding flange of the sediment collecting part is detachably fitted into and coupled with the holding groove of the holder part.

The holder part may have guide recesses on one side and the opposite side of an inner circumference of a bottom end thereof, one side and the opposite side of the holder part facing each other, and the sediment collecting part has protrusions on one side and the opposite side of an outer circumference of one end thereof, one side and the opposite side of the sediment collecting part facing each other. The protrusions of the sediment collecting part are fitted into the guide recesses of the holder part such that the holder part and the sediment collecting part are detachably coupled with each other.

Each of the guide recesses may include: an insert recess into which a corresponding protrusion of the protrusions is fitted; an anti-release recess having a predetermined angle with respect to the insert recess to prevent the corresponding protrusion from being released; and a fixing recess formed at a distal end of the anti-release recess, the corresponding protrusion being fixed to the fixing recess.

The holder part may include a lid, the lid being coupled with a top end of the holder part by means of a hinge to open and close the top end of the holder part. The lid may maintain the top end of the holder part in an open state when the apparatus for collecting surface seabed sediment moves downwardly toward a seabed and closes the top end of the holder part when the apparatus for collecting surface seabed sediment moves upwardly toward a surface of water after having collected seabed sediment.

The cover part may be formed of a stainless steel having a predetermined mass. The sediment collecting part may be formed of polyvinyl chloride or polyvinyl.

In order to achieve the above object, according to one aspect of the present invention, there is provided an apparatus for collecting seabed sediment including: a trigger; the above-described apparatus for collecting surface seabed sediment, the apparatus for collecting surface seabed sediment being connected to the trigger; and an apparatus for collecting deep seabed sediment connected to the trigger, wherein the apparatus for collecting deep seabed sediment is spaced apart from the apparatus for collecting surface seabed sediment and is configured to collect deep seabed sediment. When the apparatus for collecting surface seabed sediment is inserted into a surface seabed, the trigger apparatus is decoupled from the apparatus for collecting deep seabed sediment, such that the apparatus for collecting deep seabed sediment is inserted into a deep region of a seabed by means of free fall, whereby sediment is collected from both the surface seabed and the deep region of the seabed.

According to the present invention, the apparatus for collecting surface seabed sediment can collect sediment from a surface seabed while functioning as a trigger weight without an additional operation when collecting sediment from a deep region of the seabed.

In particular, the apparatus for collecting surface seabed sediment can fall toward a seabed in the vertical direction and be seated on the surface of the seabed in order to precisely and safely collect sediment from the surface of the seabed without causing disturbances in seabed sediment.

In addition, the apparatus for collecting seabed sediment can collect sediment from the surface of a seabed while collecting sediment from the deep seabed without disturbances.

BRIEF DESCRIPTION OF THE DRAWINGS

The above and other objects, features and advantages of the present invention will be more clearly understood from the following detailed description when taken in conjunction with the accompanying drawings, in which.

DETAILED DESCRIPTION OF THE PRESENTLY PREFERRED EMBODIMENTS

Figure 1:
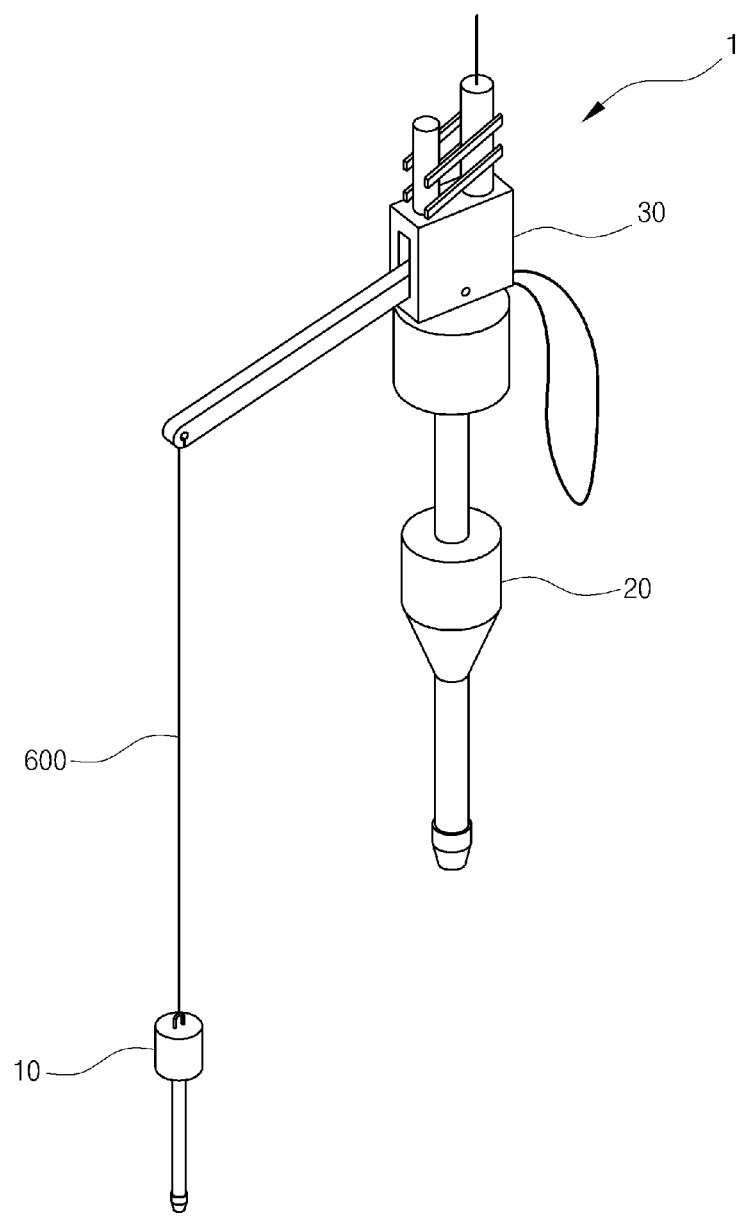
FIG. 1 is a perspective view schematically illustrating an apparatus for collecting seabed sediment according to an embodiment of the present invention.

Reference will now be made in greater detail to the present invention, embodiments of which are illustrated in the accompanying drawings. Wherever possible, the same reference numerals will be used throughout the drawings and the description to refer to the same or like parts. In the following description of the present invention, detailed descriptions of known functions and parts incorporated herein will be omitted when they may make the subject matter of the present invention unclear.

Reference will also now be made in detail to various embodiments according to the principle of the present invention, specific examples of which are illustrated in the accompanying drawings and described below, since the embodiments of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims.

It will be understood that when an element is referred to as being "coupled" or "connected" to another element, it can be directly coupled or connected to the other element or intervening elements may be present therebetween. In contrast, it should be understood that when an element is referred to as being "directly coupled" or "directly connected" to another element, there are no intervening elements present. Other expressions that explain the relationship between elements, such as "between," "directly between," "adjacent to," or "directly adjacent to," should be construed in the same way.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

FIG. 1 is a perspective view schematically illustrating an apparatus for collecting seabed sediment according to an exemplary embodiment of the present invention.

As illustrated in FIG. 1, the apparatus for collecting seabed sediment 1 according to an exemplary embodiment of the present invention includes an apparatus for collecting surface seabed sediment 10 able to collect sediment from the surface of a seabed (not illustrated), an apparatus for collecting deep seabed sediment 20 able to collect sediment from a deep region of the seabed (not illustrated), and a trigger apparatus 30.

The trigger apparatus 30 is connected to the apparatus for collecting surface seabed sediment 10 and the apparatus for collecting deep seabed sediment 20 such that the apparatuses 10 and 20 are spaced apart from each other at a predetermined distance.

When the apparatus for collecting surface seabed sediment 10 is seated on the seabed surface and subsequently is inserted into the seabed, the trigger apparatus 30 is decoupled from the apparatus for collecting deep seabed sediment 20, such that the apparatus for collecting deep seabed sediment 20 can be inserted into a deep region of the seabed by means free fall.

Descriptions of the main parts and operations of the apparatus for collecting deep seabed sediment 20 and the trigger 30 will be omitted since they are known in the art.

However, the apparatus for collecting seabed sediment 1 according to the present invention can collect surface seabed sediment using the apparatus for collecting surface seabed sediment 10, and concurrently can collect deep seabed sediment using the apparatus for collecting deep seabed sediment 20 that cooperatively works through the trigger 30 without the addition of a separate process or apparatus.

Figure 2:
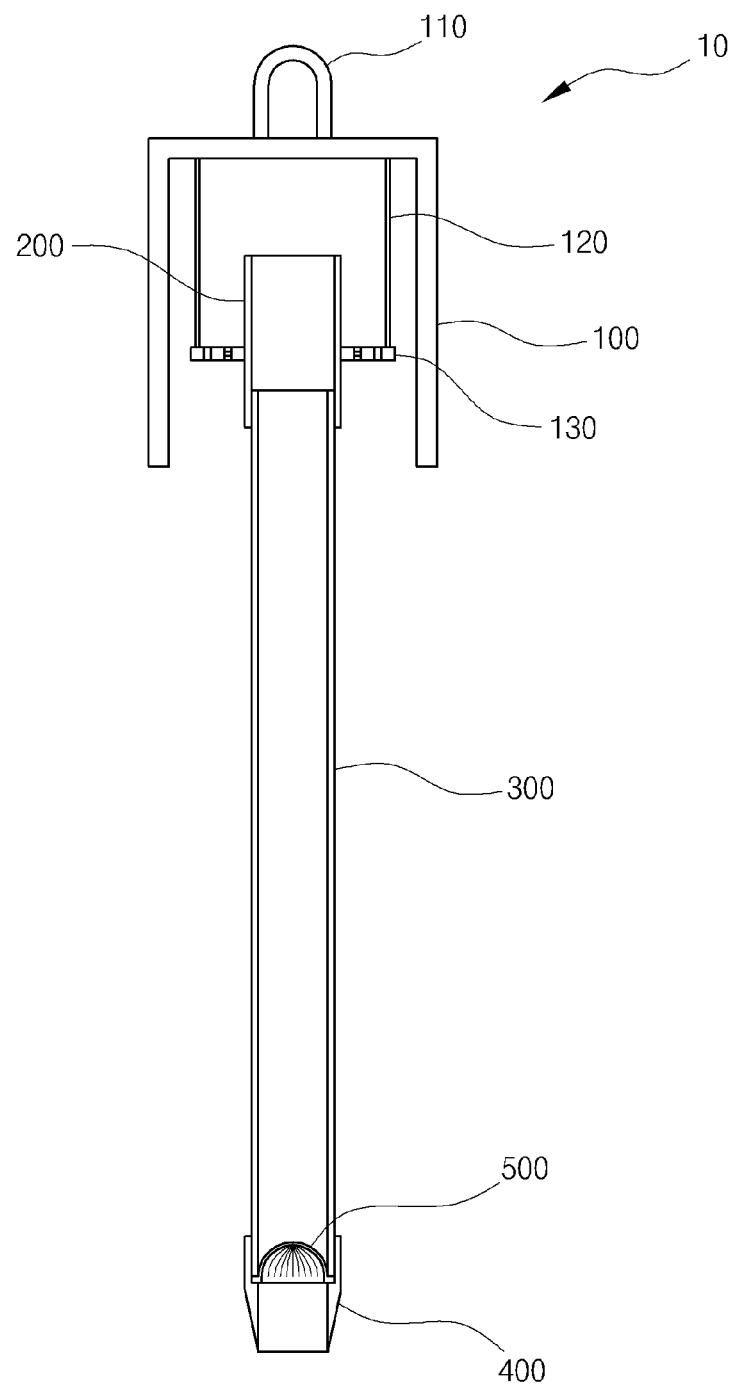
FIG. 2 is a cross-sectional view illustrating the apparatus for collecting surface seabed sediment according to an embodiment of the present invention.
Figure 3:
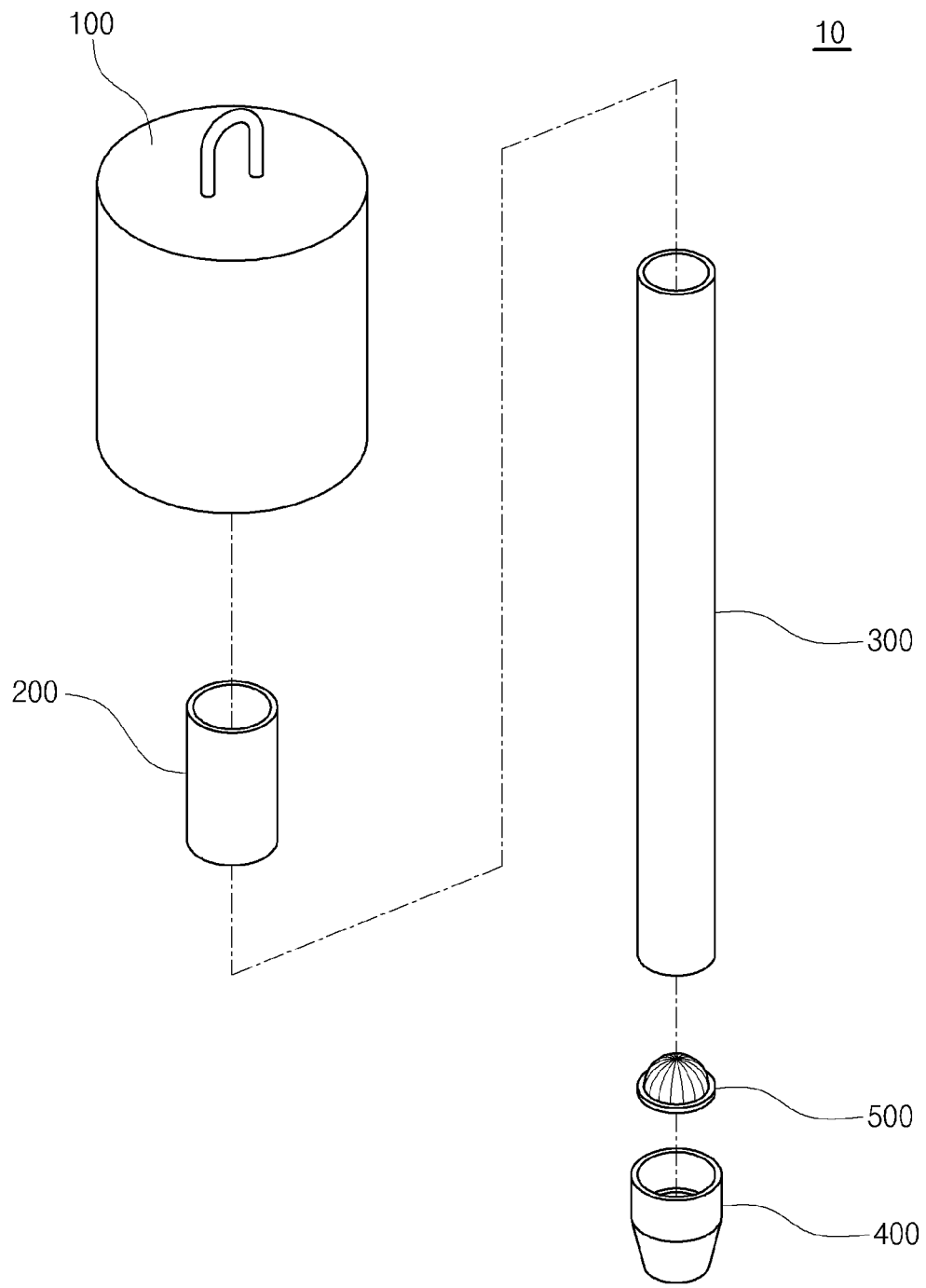
FIG. 3 is an exploded perspective view schematically illustrating the apparatus for collecting surface seabed sediment illustrated in FIG. 2.

FIG. 2 is a cross-sectional view illustrating the apparatus for collecting surface seabed sediment according to an exemplary embodiment of the present invention, and FIG. 3 is an exploded perspective view schematically illustrating the apparatus for collecting surface seabed sediment illustrated in FIG. 2.

Referring to FIG. 2 and FIG. 3, the apparatus for collecting surface seabed sediment 10 according to an exemplary embodiment of the present invention includes a cover part 100, a holder part 200, a sediment collecting part 300, a head part 400 and a catcher part 500.

The cover part 100 is connected to the trigger 30, and is in the shape of a cylinder with an open bottom end. The cover part 100 has a position maintaining part 130 disposed therein.

The cover part 100 is formed of stainless steel having a predetermined mass, such that it can act as a weight when the collecting operation is not carried out. In the case where the apparatus for collecting surface seabed sediment 10 collides against the apparatus for collecting deep seabed sediment 20, the cover part 100 can also function to protect inner parts.

Figure 4:
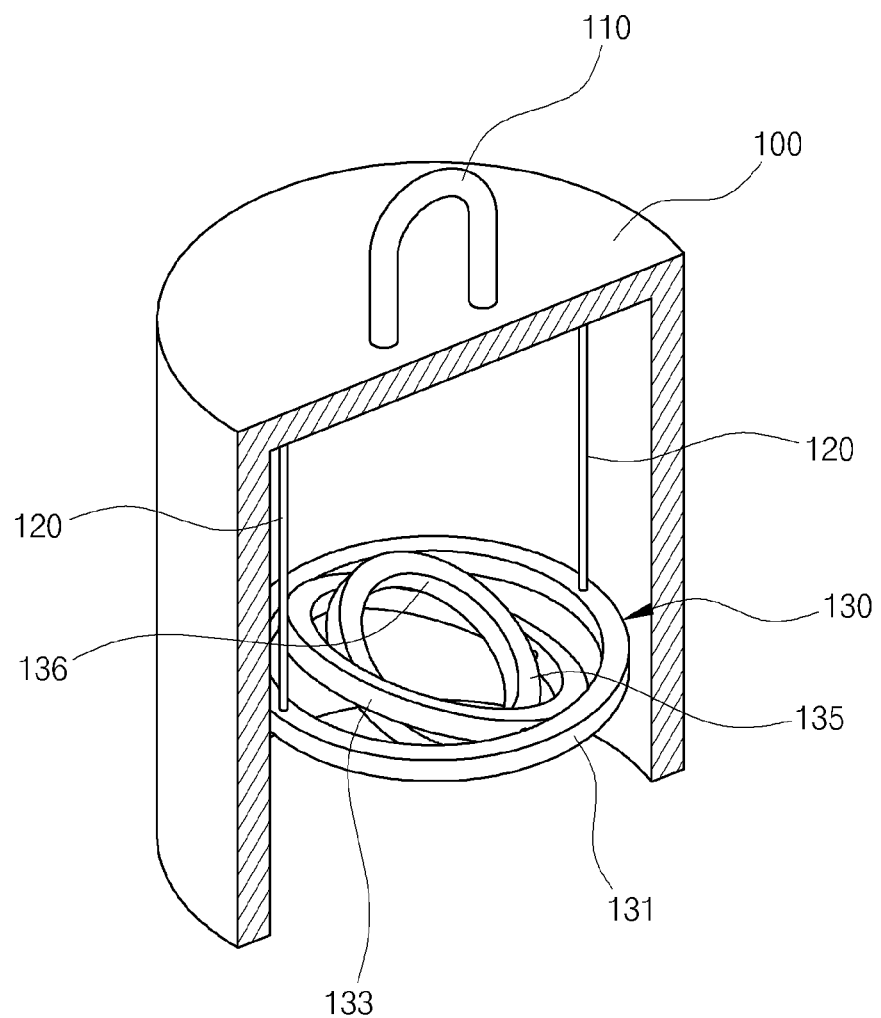
FIG. 4 is a cross-sectional view illustrating the cover part of the apparatus for collecting surface seabed sediment according to an embodiment of the present invention.
Figure 5:
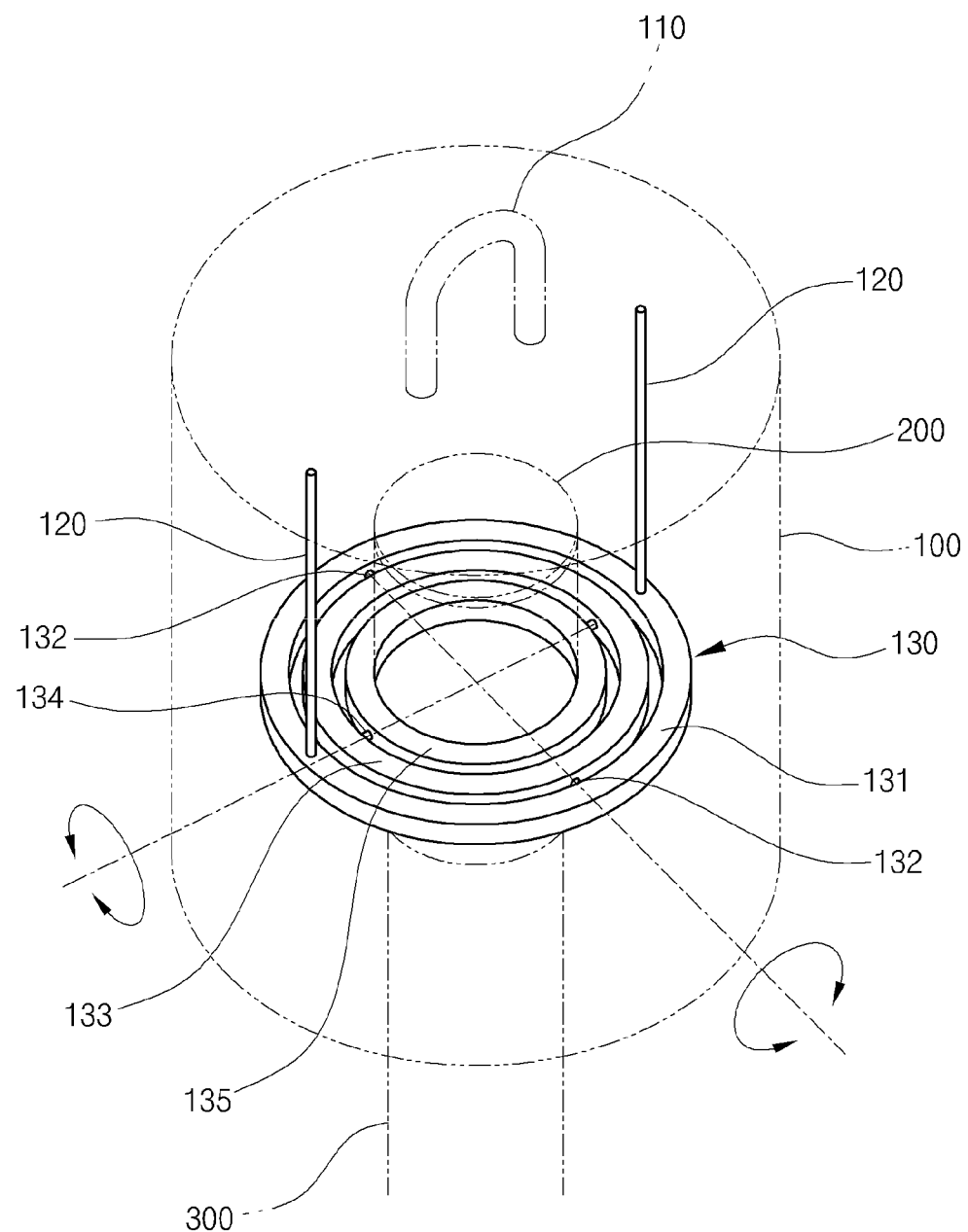
FIG. 5 is a perspective view schematically illustrating the position maintaining part of the cover part illustrated in FIG. 4.

FIG. 4 is a cross-sectional view illustrating the cover part of the apparatus for collecting surface seabed sediment according to an exemplary embodiment of the present invention, and FIG. 5 is a perspective view schematically illustrating the interior of the cover part illustrated in FIG. 4. Referring to FIG. 2 to FIG. 5, the cover part 100 has a loop member 110 on the central portion of the top end. The cover part 100 can be connected to the trigger 30 by means of the loop member 110 to which a rope or a wire is 600 engaged, as illustrated in FIG. 1.

In addition, as illustrated in FIG. 4 and FIG. 5, the cover part 100 includes a pair of support members 120 engaged with the inner surfaces of the top end of the cover part 100.

The support members 120 are spaced apart from the central portion of the cover part 100, and are disposed in the direction perpendicular to the top surface of the cover part 100. A position maintaining part 130 is connected to the other end of each of the support members 120.

The position maintaining part 130 is configured to maintain the position of the sediment collecting part 300. The position maintaining part 130 includes a circular belt member 131 that is engaged with the other end of each of the support members 120.

A first rotary member 133 having the shape of a circular belt is disposed inside the belt member 131, and is rotatably coupled with both portions of the circular belt member 131 by means of a pair of first rotary connecting members 132. A second rotary member 135 having the shape of a circular belt is disposed inside the first rotary member 133, and is rotatably coupled with both portions of the first rotary member 133 by means of a pair of second rotary connecting members 134.

In particular, the first rotary connecting member 132 and the second rotary connecting member 134 can be disposed at, for example, 90° with respect to each other such that the direction in which the first rotary member 133 rotates is perpendicular to the direction in which the second rotary member 135 rotates.

In addition, the outer circumference of the holder part 200 is engaged with the inner circumference 136 of the second rotary member 135. Accordingly, in the case where the cover part 100 is inclined or moves, the holder part 200 can always stay in position due to the directions in which the first rotary member 133 and the second rotary member 135 rotate even.

Although the coupling between the position maintaining member 130 and the holder part 200 is not specifically illustrated, the position maintaining member 130, for example, the second rotary member 135 thereof can be coupled with the holder part 200 by interference fitting or by means of a separate fixing member intended to improve fastening force.

Figure 6:
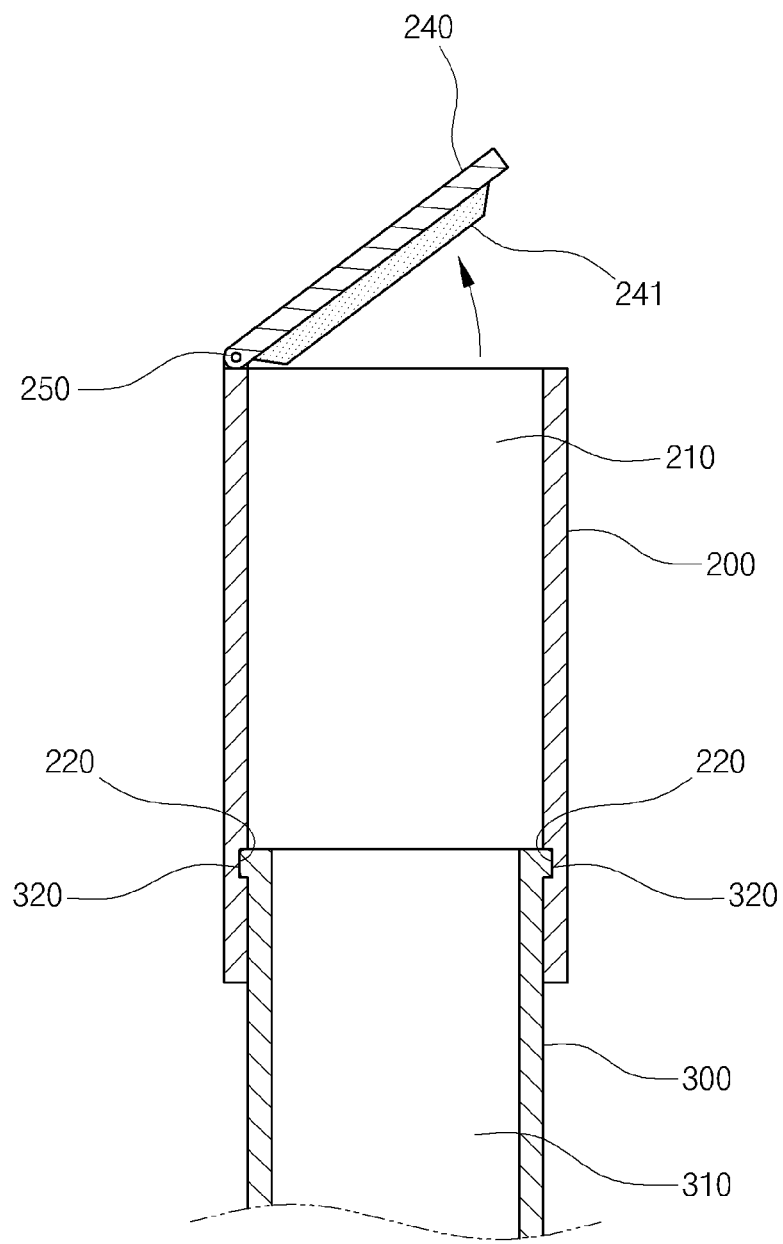
FIG. 6 illustrates the state in which the holder part and the sediment collecting part of the apparatus for collecting surface seabed sediment according to an embodiment of the present invention are connected to each other.

FIG. 6 illustrates a state in which the holder part 200 and the sediment collecting part 300 of the apparatus for collecting surface seabed sediment 100 according to an exemplary embodiment of the present invention are connected to each other.

Referring to FIG. 6, the top end or top portion of the holder part 200 is connected to the position maintaining part 130 of the cover part 100, and has a hollow space 210 that is defined therein and extends along the length thereof.

In addition, the sediment collecting part 300 is formed of polyvinyl chloride (PVC) or polyvinyl (PV), and is in the shape of pipe. One end of the sediment collecting part 300 is detachably coupled with the bottom end of the holder part 200. The sediment collecting part 300 has a receiving space 310 defined therein, such that seabed sediment can be accommodated within the receiving space 310.

The holder part 200 has a holding groove 220 on the inner circumference of the bottom end thereof, and the sediment collecting part 300 has a holding flange 320 on the outer circumference of one end thereof. The holding flange 320 of the sediment collecting part 300 is fitted into the holding groove 220 of the holder part 200, such that the holder part 200 and the sediment collecting part 300 can be detachably coupled with each other.

In addition, the holder part 200 has a lid 240 on the top end thereof. The lid 240 is coupled with the main body of the holder part 200 by means of a hinge member 250 such that the lid 240 can open and close the top end of the holder part 200. The lid 240 has a rubber packing 241 attached to the inner surface thereof, such that the lid 240 can firmly close the top end of the holder part 200.

In particular, the lid 240 can be configured such that the lid 240 maintains the top end of the holder part 200 in the open state when the apparatus for collecting surface seabed sediment 10 moves downwardly toward the seabed and closes the top end of the holder part 200 when the apparatus for collecting surface seabed sediment 10 moves upwardly toward the surface of the water after having collected seabed sediment.

Figure 7:
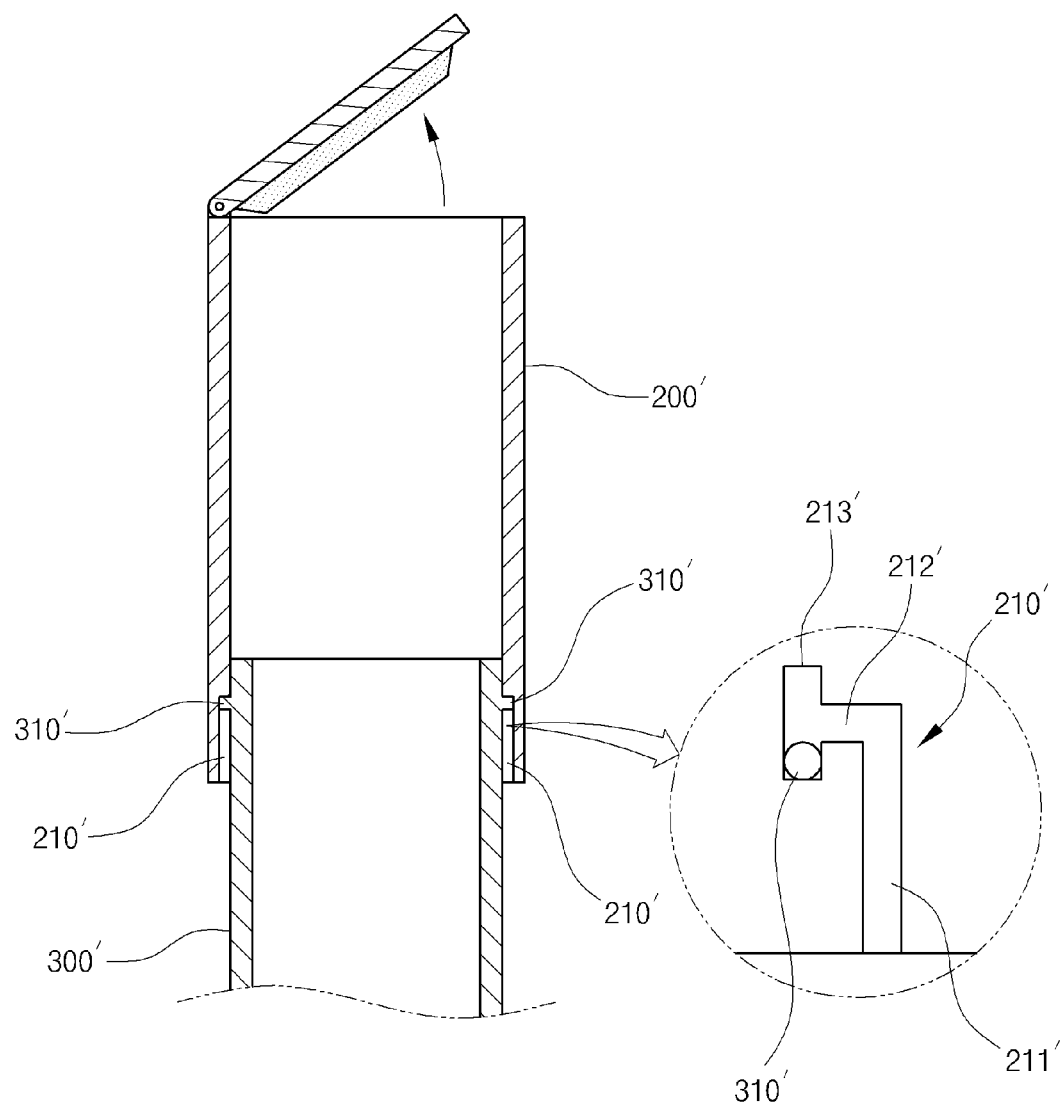
FIG. 7 illustrates the state in which the holder part and the sediment collecting part of the apparatus for collecting surface seabed sediment according to an embodiment of the present invention are connected to each other.

FIG. 7 illustrates another state in which the holder part 200' and the sediment collecting part 300' are connected to each other. As illustrated in FIG. 7, the holder part 200' has guide recesses 210' on one side and the opposite side of the inner circumference of the bottom end thereof, one side and the opposite side facing each other. The sediment collecting part 300' has protrusions 310' on one side and the opposite side of the outer circumference of one end thereof, one side and the opposite side facing each other. The protrusions 310' are formed at positions corresponding to the guide recesses 210'.

Each of the guide recesses 210' has an insert recess 211', an anti-release recess 212' and a fixing recess 213'. A corresponding protrusion 310' is fitted into the insert recess 211'. The anti-release recess 212' continuously extends from the insert recess 211' at a predetermined angle (e.g. 90°) to prevent the protrusion 310' from being released. The fixing recess 213' is formed at the distal end of the anti-release recess 212', and the protrusion 310' is fixed to the fixing recess 213'.

Accordingly, the protrusions 310' of the sediment collecting part 300' are fitted into the guide recesses 210' of the holder part 200', such that the sediment collecting part 300' and the holder part 200' can be detachably coupled with each other.

In addition, although not specifically illustrated, the holder part and the sediment collecting part according to the present invention may employ a coupling method such as one-touch fitting.

Figure 8:
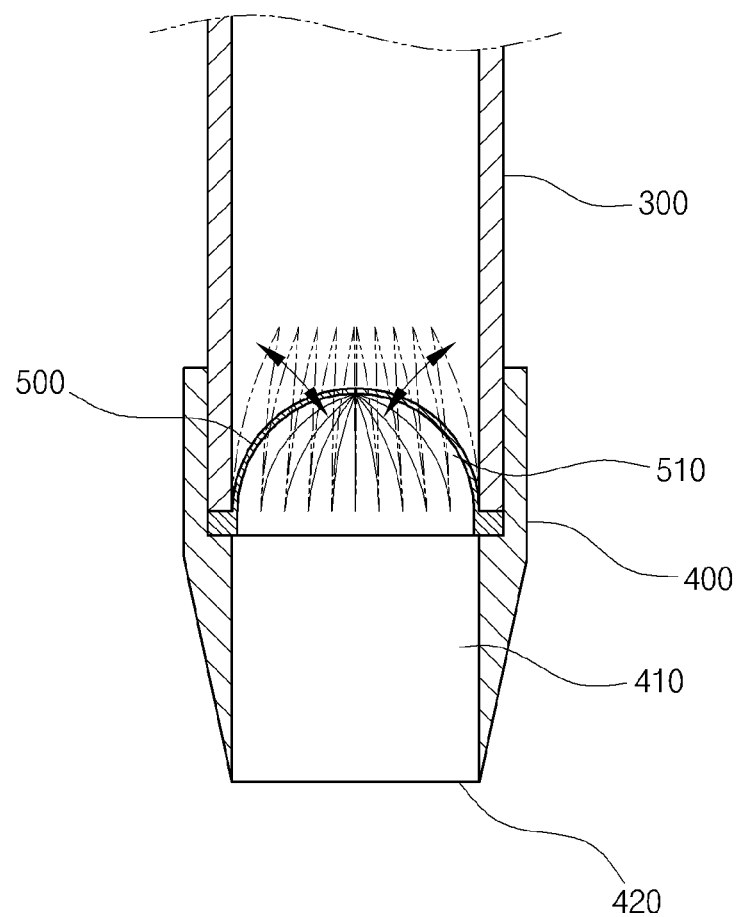
FIG. 8 illustrates the state in which the sediment collecting part and the head part of the apparatus for collecting surface seabed sediment 10 according to the present invention are connected to each other.

FIG. 8 illustrates a state in which the sediment collecting part and the head part of the apparatus for collecting surface seabed sediment 10 according to the present invention are connected to each other.

As illustrated in FIG. 8, one end of the head part 400 can be fitted into the other end (bottom end) of the sediment collecting part 300.

The head part 400 has a hollow space 410 defined therein and an insert blade 420 at the outer periphery of the other end thereof. The insert blade 420 enables the sediment collecting part 300 to be easily inserted into the surface seabed to collect sediment.

In addition, the catcher part 500 is disposed between the sediment collecting part 300 and the head part 400, i.e. on the inner circumference of the head part 400.

As illustrated in FIG. 8, the catcher part 500 has a plurality of elastic pieces 510 that are convex and protrude toward the sediment collecting part 300 to form a basket-shaped structure. In the state in which the elastic pieces 510 are open due to the elasticity thereof, seabed sediment is allowed to enter the receiving space 310 of the sediment collecting part 300. When the apparatus for collecting surface seabed sediment 10 is pulled upwards (moved upwards to the surface of the water)

after the collection of sediment, the elastic pieces 510 are closed to prevent the collected sediment from being lost.

Figure 9:
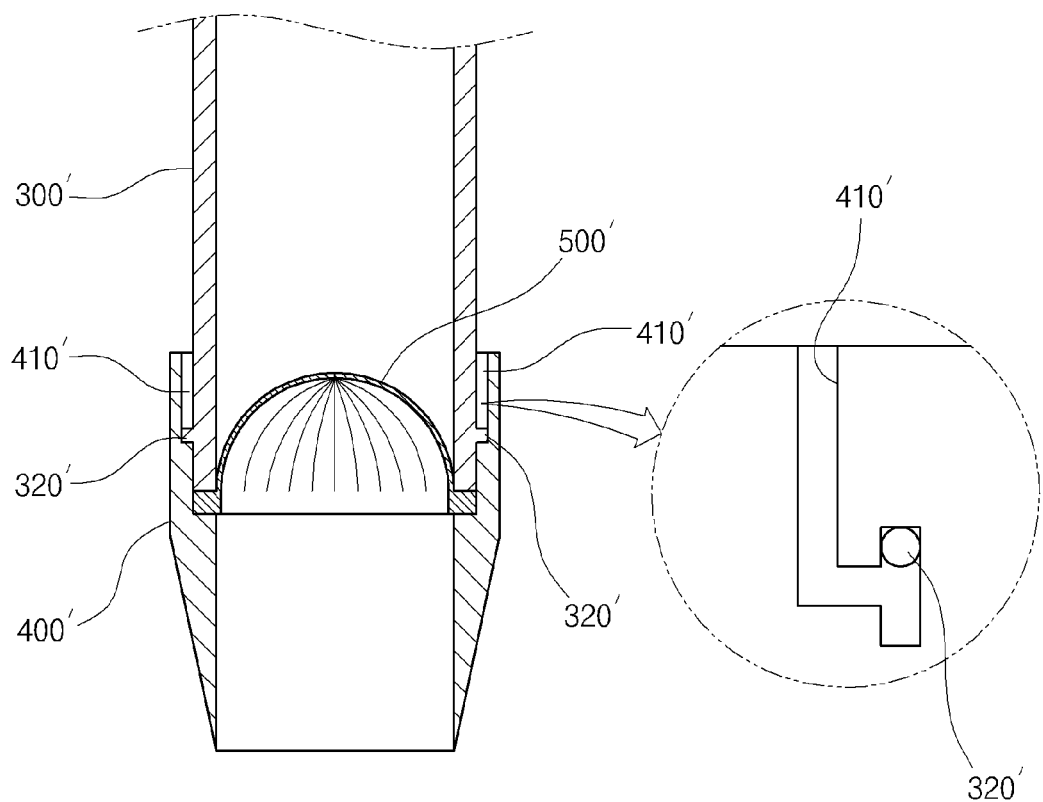
FIG. 9 illustrates the state in which the sediment collecting part and the head part of the apparatus for collecting surface seabed sediment 10 according to the present invention are connected to each other.

FIG. 9 illustrates another state in which the sediment collecting part 300' and the head part 400' are connected to each other.

A description of the catcher part 500' disposed between the sediment collecting part 300 and the head part 400' will be omitted since the catcher part 500' has the same configuration as the catcher part 500 illustrated in FIG. 8.

As illustrated in FIG. 9, the head part 400' has guide recesses 410' on one side and the opposite side of the inner circumference of the top end thereof, one side and the opposite side facing each other. The sediment collecting part 300' has protrusions 320' on one side and the opposite side of the outer circumference of the other end (bottom end) thereof, one side and the opposite side facing each other. The protrusions 320' are formed at positions corresponding to the guide recesses 410'.

The guide recesses 410' formed in the head part 400' have the same shape as the guide recesses 210' formed in the head part 200' illustrated in FIG. 7, and the coupling relationship between the protrusions 320' and the guide recesses 510' is the same as that of the corresponding parts. Accordingly, detailed description of these parts will be omitted.

Accordingly, the sediment collecting part 300' and the head part 500' can be detachably coupled with each other. In addition, the holder part and the sediment collecting part according to the present invention may be coupled with each other by a variety of coupling methods such as one-touch fitting.

Although the exemplary embodiments of the present invention have been described for illustrative purposes, those skilled in the art will appreciate that various modifications, additions and substitutions are possible, without departing from the scope and spirit of the present invention as disclosed in the accompanying claims.

What is claimed is:

1. An apparatus for collecting surface seabed sediment comprising:
    a cylindrical cover part connected to a trigger, the cylindrical cover part having (a) an open bottom end, (b) a pair of support members, where a first end of each of the support members is engaged with an inner surface of a top end of the cylindrical cover part and where the support members are spaced apart from a central portion of the cylindrical cover part and disposed in a direction perpendicular to the top surface of the cylindrical cover part, and (c) a position maintaining part disposed at a second end of each of the support members;
    a holder part coupled with the position maintaining part, the holder part having a longitudinal hollow space defined therein;
    a pipe-shaped sediment collecting part including (a) a first end detachably coupled with the position maintaining part via a holder part and arranged such that a longitudinal direction of the pipe-shaped sediment collecting part is in a direction of the force of gravity, and (b) a receiving space defined therein, the receiving space configured to receive seabed sediment;
    a head part including, (a) an end disposed on a second end of the pipe-shaped sediment collecting part, (b) a hollow space defined therein, and (c) an insert blade on a periphery of the head part, the insert blade configured to insert the head part into a surface of a seabed; and
    a catcher part on an inner circumference of the head part, the catcher part configured to allow seabed sediment to be received by the receiving space of the pipe-shaped sediment collecting part while preventing the collected seabed sediment from exiting the pipe-shaped collecting part.

2. The apparatus according to claim 1, further comprising:
    a circular belt member engaged with the second end of each of the support members;
    a first rotary member inside the circular belt member, the first rotary member rotatably coupled with opposite portions of the circular belt member; and
    a second rotary member inside the first rotary member, the second rotary member rotatably coupled with opposite portions of the first rotary member,
    wherein,
        a direction in which the first rotary member rotates is perpendicular to a direction in which the second rotary member rotates, and
        an outer circumference of the holder part is coupled with an inner circumference of the second rotary member.

3. The apparatus according to claim 1, wherein:
    the holder part has a holding groove on an inner circumference of a bottom end thereof,
    the pipe-shaped sediment collecting part includes a holding flange on an outer circumference of the first end and
    the holding flange of the pipe-shaped sediment collecting part is detachably fitted into and coupled with the holding groove of the holder part.

4. The apparatus according to claim 1, wherein:
    a bottom end of the holder part has guide recesses on first and second sides, the first and second sides located on an inner circumference of the bottom end of the holder part and facing each other, and
    the pipe-shaped sediment collecting part includes protrusions on first and second sides located on an outer circumference of the first end of the pipe-shaped sediment collecting part, the first and second sides of the pipe-shaped sediment collecting part facing each other, and
    the protrusions of the pipe-shaped sediment collecting part configured to fit into the guide recesses of the holder part such that the holder part and the sediment collecting part are detachably coupled with each other.

5. The apparatus according to claim 4, wherein each of the guide recesses comprises:
    an insert recess configured to receive a corresponding protrusion on the pipe-shaped sediment collecting part;
    an anti-release recess having a predetermined angle with respect to the insert recess and configured to prevent the corresponding protrusion on the pipe-shaped sediment collecting part from being released from the insert recess; and
    a fixing recess formed at a distal end of the anti-release recess, the corresponding protrusion on the pipe-shaped sediment collecting part being fixed to the fixing recess.

6. The apparatus according to claim 1, wherein:
    the holder part comprises a lid coupled with a top end of the holder part via a hinge to open and close the top end of the holder part, and
    the lid configured to (a) maintain the top end of the holder part in an open state when the apparatus for collecting surface seabed sediment moves downwardly toward a seabed and (b) close the top end of the holder part when the apparatus for collecting surface seabed sediment moves upwardly toward a surface of water.

7. The apparatus according to claim 1, wherein the cover part is stainless steel.

8. The apparatus according to claim 1, wherein the sediment collecting part is polyvinyl chloride or polyvinyl.

9. The apparatus for collecting seabed sediment according to claim 1 further comprising:
a trigger;
the apparatus for collecting surface seabed sediment connected to the trigger; and
an apparatus for collecting deep seabed sediment connected to the trigger,
wherein,
the apparatus for collecting deep seabed sediment is spaced apart from the apparatus for collecting surface seabed sediment, and
the trigger is configured to decouple from the apparatus for collecting deep seabed sediment when the apparatus for collecting surface seabed sediment is inserted into a surface seabed, such that the apparatus for collecting deep seabed sediment is inserted into a deep region of a seabed by means of free fall, and whereby sediment is collected from both the surface seabed and the deep region of the seabed.

* * * * *